United States Patent [19]

Nonomura et al.

[11] Patent Number: 5,760,065
[45] Date of Patent: Jun. 2, 1998

[54] ANTI-HIV AGENT

[75] Inventors: Yoshiaki Nonomura, Tokyo, Japan; Hiroyuki Sasaki, Bryn Mawr, Pa.; Hideaki Karaki; Nobuhiro Fusetani, both of Tokyo, Japan

[73] Assignee: Kyowa Hakko Kogyo Co., Ltd., Tokyo, Japan

[21] Appl. No.: 640,741

[22] PCT Filed: Sep. 13, 1995

[86] PCT No.: PCT/JP95/01819

§ 371 Date: May 6, 1996

§ 102(e) Date: May 6, 1996

[87] PCT Pub. No.: WO96/08478

PCT Pub. Date: Mar. 21, 1996

[30] Foreign Application Priority Data

Sep. 13, 1994 [JP] Japan .................. 6-218486

[51] Int. Cl.[6] .................................. A61K 31/42
[52] U.S. Cl. ............................... 514/374; 514/375
[58] Field of Search ........................ 514/375, 374

[56] References Cited

PUBLICATIONS

The 67th Annual Meeting of the Japanese Pharmacological Society (1994) 263p pp. 3–65 Masahi et al.
The 67th Annual Meeting of the Japanese Pharmacological Society (1994) 205p pp. 2–157 Botkyung et al.
The 113th Meeting of the Japanese Society of Veterinary Science (1992) 94.
Tetrahedron Letters, vol. 30, No. 21 pp. 2809–2812 (1989) Fusetari et al.
J. Org. Chem. Vo. 54, pp. 1360–1363 (1989).
J. Am. Chem. vol. 108, pp. 847–849 (1986).
J. Am. Chem. Soc. vol. 108, pp. 846–847 (1986).
J. Org. Chem. vol. 53, pp. 5014–5020 (1988).
Journal of National Products, vol. 56, No. 5, pp. 787–791 (1993).
Tetrahedron Letters, vol. 28, No. 25, pp. 2809–2812 (1987).

*Primary Examiner*—Russell Travers
*Attorney, Agent, or Firm*—Antonelli, Terry, Stout & Kraus, LLP

[57] ABSTRACT

The present invention relates to an anti-HIV agent which comprises, as an active ingredient, Mycalolide B represented by formula (Ia):

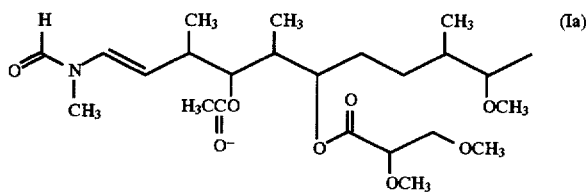

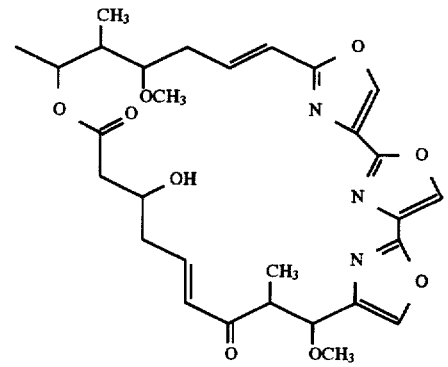

or the like.

4 Claims, No Drawings

1
ANTI-HIV AGENT

TECHNICAL FIELD

The present invention relates to a novel anti-human immunodeficiency virus (HIV) agent which has HIV proliferation inhibitory activity.

BACKGROUND ART

HIV is the causative virus of acquired immune deficiency syndrome (AIDS). The virus infects helper T cells and proliferates therein to rupture the cells. As a result, cell-mediated immune deficiency is induced, which leads to the manifestation of AIDS.

Azidothymidine (AZT) and some other substances are currently known as anti-HIV agents.

The life cycle of HIV comprises binding, entry, uncoating, reverse transcription, integration, transcription, protein synthesis, modification, assembly, trafficking, and budding. The action of AZT as an anti-HIV agent is attributed to inhibition of reverse transcription peculiar to viruses.

On the other hand, it is known that Mycalolide B represented by formula (Ia):

2
DISCLOSURE OF THE INVENTION

The present inventors selected the step of intracellular transportation (trafficking) of virus particles in the life cycle of HIV as the step at which the metabolism of HIV can be inhibited without affecting the metabolism of host cells. As a result of search, it has been found that the compounds having the structure shown below inhibit the trafficking of HIV and thus inhibit the proliferation of HIV, and the present invention has been completed.

The present invention relates to an anti-human immunodeficiency virus (HIV) agent which comprises, as an active ingredient, a compound represented by formula (I):

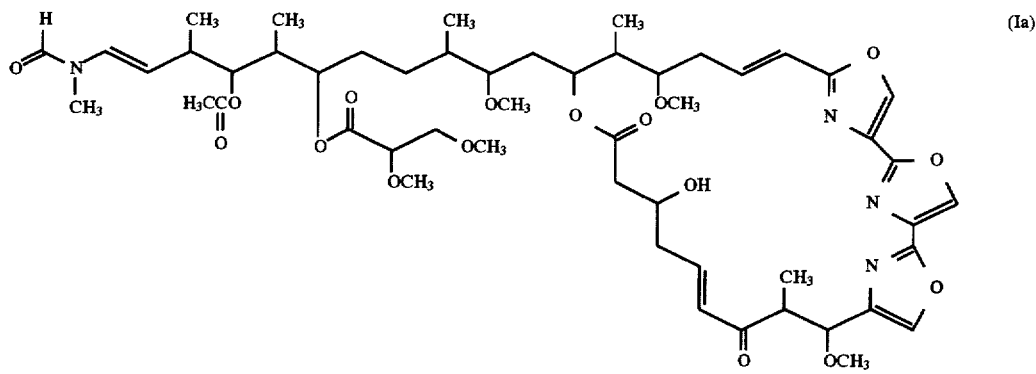

(Ia)

has actin polymerization inhibitory activity [the 67th Annual Meeting of the Japanese Pharmacological Society (1994)], anti-platelet activity [the 67th Annual Meeting of the Japanese Pharmacological Society (1994)], and inhibitory activity against contraction of smooth muscle [the 113th Meeting of the Japanese Society of Veterinary Science (1992)].

It is desired to develop anti-HIV agents which are excellent in effectiveness and have little side effect.

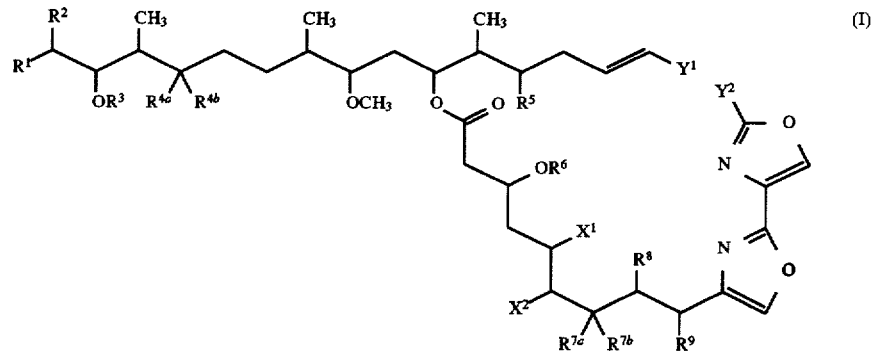

(I)

wherein $R^1$ represents

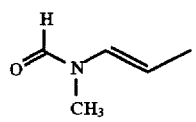

or carboxymethyl; $R^2$ represents hydrogen or lower alkyl; $R^3$ represents lower alkanoyl or lower alkyl; $R^{4a}$ represents hydrogen, and $R^{4b}$ represents

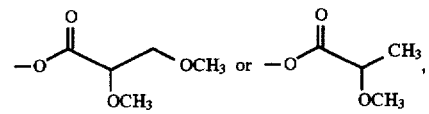

or $R^{4a}$ and $R^{4b}$ together represent oxygen; $R^5$ represents hydrogen, hydroxy, or lower alkoxy; $R^6$ represents hydrogen, carbamoyl, or lower alkanoyl; $R^{7a}$ represents hydrogen, and $R^{7b}$ represents hydroxy, or $R^{7a}$ and $R^{7b}$ together represent oxygen; $R^8$ represents hydrogen, lower alkyl, or hydroxymethyl; $R^9$ represents lower alkoxy or lower alkyl; $X^1$ represents hydrogen or hydroxy, and $X^2$ represents hydrogen, or $X^1$ and $X^2$ together represent a single bond; and $Y^1$ represents lower alkoxycarbonyl, and $Y^2$ represents carbamoyl, or $Y^1$ and $Y^2$ together represent, as $-Y^1-Y^2-$,

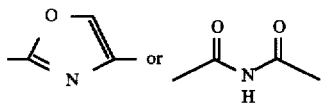

[hereinafter referred to as Compound (I)].

The present invention also relates to a method for treating AIDS by administering an effective amount of a compound represented by formula (I) or a pharmaceutically acceptable salt thereof.

Further, the present invention relates to the use of a compound represented by formula (I) or a pharmaceutically acceptable salt thereof for the preparation of pharmaceutical compositions useful for treating AIDS.

In the definitions of the groups in formula (I), the lower alkyl and the lower alkyl moiety of the lower alkanoyl, the lower alkoxy and the lower alkoxycarbonyl mean a straight-chain or branched alkyl group having 1 to 6 carbon atoms such as methyl, ethyl, propyl, isopropyl, butyl, isobutyl, sec-butyl, tert-butyl, pentyl, neopentyl and hexyl.

Representative examples of Compound (I) are shown in Table 1 with structural formulae.

TABLE 1 (1)

| Compound | $R^2$ | $R^3$ | $R^{4a}$ | $R^{4b}$ | $R^5$ |
|---|---|---|---|---|---|
| Mycalolide A | $CH_3$ | $CH_3CO$ | O | | $OCH_3$ |
| Mycalolide B | $CH_3$ | $CH_3CO$ | H | (-O-C(=O)-CH(OCH_3)-CH_2-OCH_3) | $OCH_3$ |
| Mycalolide C | $CH_3$ | $CH_3CO$ | H | (-O-C(=O)-CH(OCH_3)-CH_3) | $OCH_3$ |
| Halichondramide | H | $CH_3$ | O | | H |
| Jaspisamide B | H | $CH_3$ | O | | OH |
| Jaspisamide C | $CH_3$ | $CH_3$ | O | | H |

TABLE 1 (2)

(structure I)

| Compound | R⁵ | R⁶ | R⁸ |
|---|---|---|---|
| Kabiramide A | OCH₃ | CONH₂ | CH₂OH |
| Kabiramide B | OH | CONH₂ | CH₃ |
| Kabiramide C | OCH₃ | CONH₂ | CH₃ |
| Kabiramide D | OCH₃ | H | CH₃ |
| Kabiramide E | OCH₃ | COCH₃ | CH₃ |
| Tetrahydro halichondramide | H | H | CH₃ |

TABLE 1 (3)

(structure I)

| Compound | R² | R³ | R⁴ᵃ R⁴ᵇ | R⁵ | R⁸ | R⁹ | X¹ |
|---|---|---|---|---|---|---|---|
| 33-Methyldihydro halichondramide | CH₃ | CH₃ | O | H | CH₃ | OCH₃ | H |
| Ulpualide A | CH₃ | CH₃CO | O | OCH₃ | H | CH₃ | H |
| Ulpualide B | CH₃ | CH₃CO | H, —O—C(=O)—CH(OCH₃)—CH₂OCH₃ | OCH₃ | H | CH₃ | H |
| Dihydro halichondramide | H | CH₃ | O | H | CH₃ | OCH₃ | H |
| Jaspisamide A | H | CH₃ | O | H | CH₃ | OCH₃ | OH |

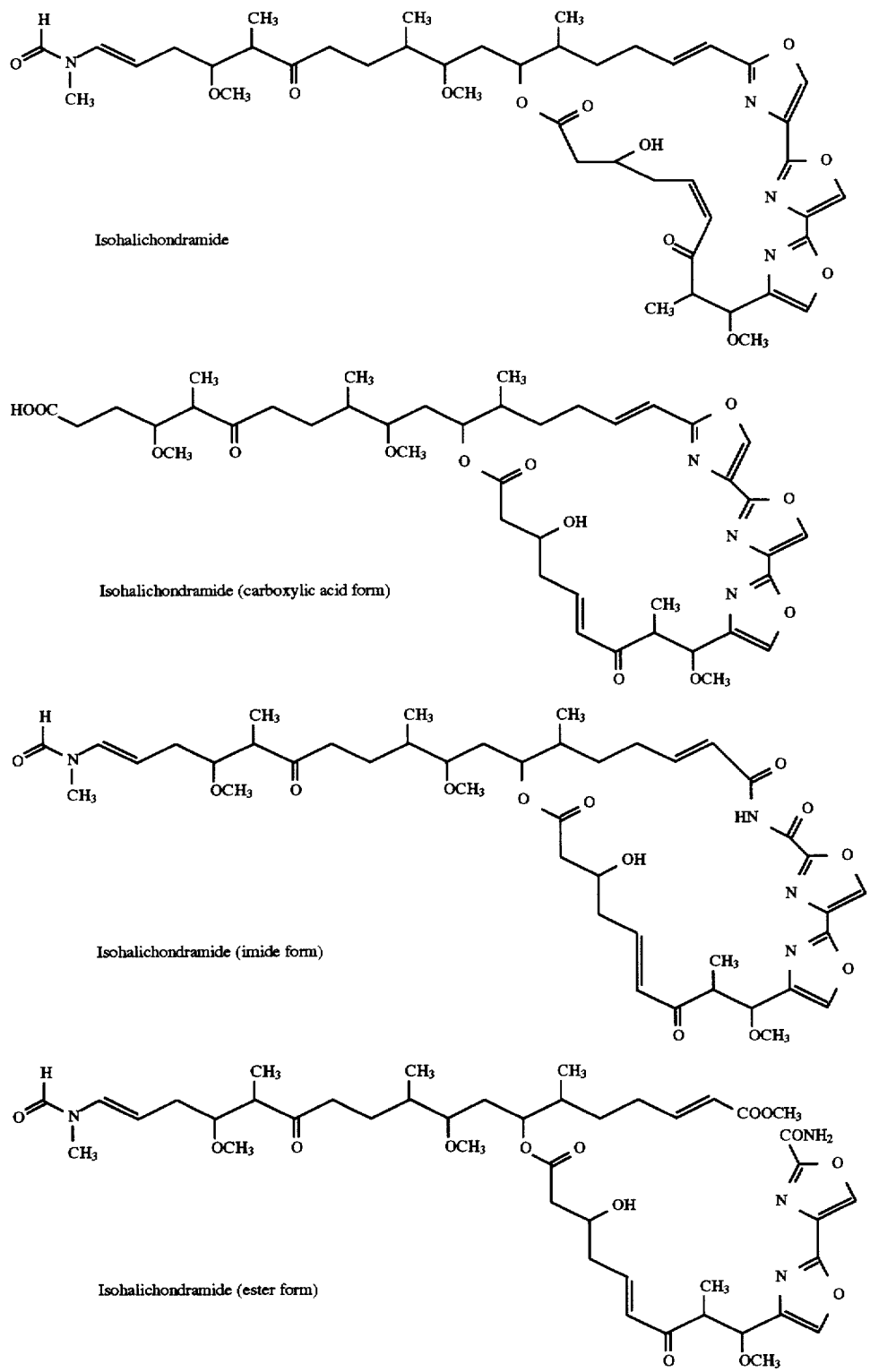

Isohalichondramide

Isohalichondramide (carboxylic acid form)

Isohalichondramide (imide form)

Isohalichondramide (ester form)

Mycalolide A, B and C, which have cytotoxicity and antifungal activity, can be obtained by isolation and purification from Mycale sp. [Tetrahedron Lett., 30, 2809 (1989)].

Kabiramide A, B, D and E and 33-Methyldihydrohalichondramide, which have cytotoxicity, can be obtained by isolation and purification from egg masses of Hexabranchus sp. [J. Org. Chem., 54, 1360 (1989)].

Kabiramide C, which has antifungal activity, can be obtained by isolation and purification from egg masses of Nudibranch [J. Am. Chem. Soc., 108, 847 (1986)].

Ulpualide A and B, which have cytotoxicity and antibacterial activity, can be obtained by isolation and purification from egg masses of *Hexabranchus sanguineus* [J. Am. Chem. Soc., 108, 846 (1986)].

Halichondramide, Dihydrohalichondramide, Isohalichondramide, Isohalichondramide (carboxylic acid form), Isohalichondramide (imide form) and Isohalichondramide (ester form), which have cytotoxicity and antifungal activity, can be obtained by isolation and purification from *Halichondria sp.* [J. Org. Chem., 53, 5014 (1988)].

Tetrahydrohalichondramide, which has cytotoxicity and antifungal activity, can be obtained by isolation and purification from egg masses of *Hexabranchus sanguineus* [J. Org. Chem., 53, 5014 (1988)].

Jaspisamide A, B and C, which have cytotoxicity, can be obtained by isolation and purification from *Jaspis sp.* [J. Nat. Prod., 56, 787 (1993)].

The pharmacological activity of Compound (I) is described below referring to Test Example.

Test Example

U937 cells (derived from human lymphocytes) infected with HIV (type $III_B$) were cultured in RPMI-1640 medium (Biocell Laboratories) containing Test Compound (I) and 10% fetal bovine serum (FBS) at 37° C. for 15 minutes in a $CO_2$-incubator. The cultured U937 cells were washed with RPMI-1640 medium and then cultured in RPMI-1640 medium containing 10% FBS at 37° C. for 6 hours in the $CO_2$-incubator. The degree of inhibition of HIV budding by the test compound was evaluated by the reverse transcriptase activity in a unit culture. Cytotoxicity test was carried out by the MTT method [J. Immunol. Method., 65, 55 (1983)].

The results are shown in Table 2.

TABLE 2

| Test Compound | Concentration (M) | HIV Proliferation Inhibitory Activity (%) | Cytotoxicity (%) |
|---|---|---|---|
| Mycalolide B | $10^{-10}$ | 14.3 | 0.7 |
| " | $10^{-9}$ | 28.6 | 1.5 |
| " | $10^{-8}$ | 57.1 | 2.2 |
| " | $10^{-7}$ | 71.4 | 4.3 |

It is expected from the above results that the anti-HIV agent of the present invention has a potent inhibitory activity against HIV proliferation and has little harmful effect on host cells at effective concentrations.

Compound (I) and pharmaceutically acceptable salts thereof may be orally or non-orally administered as they are or in the form of various pharmaceutical compositions. Examples of the pharmaceutical compositions are tablets, pills, powders, granules, capsules, suppositories and injections.

These compositions can be prepared by employing methods conventionally used and may be formulated to contain various excipients, lubricants, binders, disintegrators, suspending agents, isotonicity agents, emulsifiers, absorption facilitators, and the like.

Examples of the carriers used for preparing the pharmaceutical compositions include water, distilled water for injection, physiological saline, glucose, fructose, sucrose, mannitol, lactose, starch, corn starch, potato starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resin, sorbitan fatty acid ester and glycerin fatty acid ester, which are appropriately selected according to the kind of composition.

The dose of Compound (I) to be used for the above purpose will be determined by the desired therapeutic effect, the administration route, the administration period, the age and body weight of a patient, etc. It is generally appropriate to administer Compound (I) orally or non-orally (e.g. by injection, drip infusion, rectal administration of suppositories, and application of patch to the skin) to an adult in a daily dose of 0.01–2 mg/kg.

The mode of operation of the present invention is described below by Examples.

Best Mode for Carrying Out the Invention

EXAMPLE 1

Tablets

| Mycalolide B | 100 g |
|---|---|
| Lactose | 40 g |
| Corn starch | 18 g |
| Calcium carboxymethyl cellulose | 10 g |

A mixture of the above ingredients is kneaded with 42 ml of a 10% hydroxypropyl cellulose solution. The kneaded mixture is granulated by using an extruding granulator equipped with a basket of 1.0 mm meshes, followed by addition of magnesium stearate to prepare granules for tabletting. Tablets of 8 mm diameter each weighing 170 mg and containing 100 mg of Mycalolide B are obtained in a conventional manner.

EXAMPLE 2

Capsules

| Mycalolide B | 50 g |
|---|---|
| Lactose | 80 g |
| Potato starch | 38 g |

A mixture of the above ingredients is kneaded with 42 ml of a 10% hydroxypropyl cellulose solution. The kneaded mixture is granulated in the same manner as in Example 1, followed by addition of magnesium stearate. Capsules each weighing 170 mg and containing 50 mg of Mycalolide B are obtained in a conventional manner.

EXAMPLE 3

Soft Capsules

Mycalolide B (10 g) is dissolved in 100 g of soybean oil, and the resulting solution is loaded into capsules in a conventional manner to prepare soft capsules each containing 10 mg of Mycalolide B.

Industrial Applicability

The present invention provides an excellent anti-HIV agent.

We claim:

1. A method for treating AIDS comprising the steps of selecting a patient infected with HIV; and administering an effective amount of a compound having anti-HIV activity represented by formula (I):

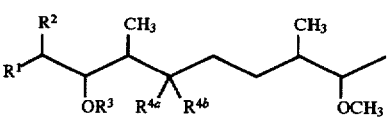

-continued

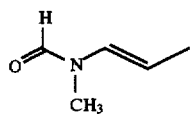

wherein $R^1$ represents

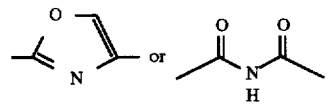

or carboxymethyl; $R^2$ represents hydrogen or lower alkyl; $R^3$ represents lower alkanoyl or lower alkyl; $R^{4a}$ represents hydrogen, and $R^{4b}$ represents or $R^{4a}$ and $R^{4b}$ together represent oxygen; $R^5$ represents hydrogen, hydroxy, or lower alkoxy; $R^6$ represents hydrogen, carbamoyl, or lower alkanoyl; $R^{7a}$ represents hydrogen, and $R^{7b}$ represents hydroxy, or $R^{7a}$ and $R^{7b}$ together represent oxygen; $R^8$ represents hydrogen, loweralkyl, or hydroxymethyl; $R^9$ represents lower alkoxy or lower alkyl; $X^1$ represents hydrogen or hydroxy, and $X^2$ represents hydrogen, or $X^1$ and $X^2$ together represent a single bond; and $Y^1$ represents lower alkoxycarbonyl, and $Y^2$ represents carbamoyl, or $Y^1$ and $y^2$ together represents, as $-Y^1-Y^2-$, or a pharmaceutically acceptable salt thereof.

2. A method of treating AIDS according to claim 1 wherein said compound of formula (I) has reverse transcriptase inhibitory activity.

3. A method of treating AIDS which comprises the steps of: selecting a patient infected with HIV; and administering an effective amount of a compound having anti-HIV activity represented by formula (Ia):

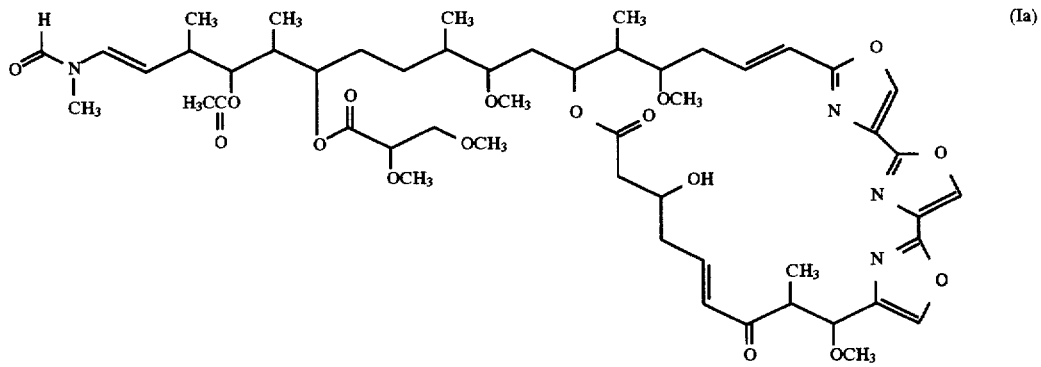

or a pharmaceutically acceptable salt thereof.

4. A method of treating AIDS according to claim 3 wherein said compound of formula (Ia) has reverse transcriptase inhibitory activity.

* * * * *